US008124115B2

(12) United States Patent
Veeger et al.

(10) Patent No.: US 8,124,115 B2
(45) Date of Patent: *Feb. 28, 2012

(54) ALCOHOLIC PUMP FOAM

(75) Inventors: Marcel Veeger, Goch (DE); Markus Himming, Oberhausen (DE)

(73) Assignee: DEP IP Limited (GB)

( * ) Notice: Subject to any disclaimer, the term of this patent is extended or adjusted under 35 U.S.C. 154(b) by 0 days.

This patent is subject to a terminal disclaimer.

(21) Appl. No.: 12/624,073

(22) Filed: Nov. 23, 2009

(65) Prior Publication Data

US 2010/0069505 A1  Mar. 18, 2010

Related U.S. Application Data

(63) Continuation of application No. 11/312,559, filed on Dec. 21, 2005, now Pat. No. 7,670,615.

(30) Foreign Application Priority Data

Dec. 21, 2004 (DE) .......................... 10 2004 062 775

(51) Int. Cl.
*A01N 25/00* (2006.01)
*A01N 31/00* (2006.01)
*A01N 31/14* (2006.01)
*A01N 43/04* (2006.01)
*A01N 55/00* (2006.01)
*A61K 31/045* (2006.01)
*A61K 8/34* (2006.01)

(52) U.S. Cl. ............ 424/405; 514/25; 514/63; 514/715; 514/724; 514/738; 514/781

(58) Field of Classification Search .................... 424/405
See application file for complete search history.

(56) References Cited

U.S. PATENT DOCUMENTS

| | | | |
|---|---|---|---|
| 2,054,989 A | 9/1936 | Moore |
| 2,559,749 A | 7/1951 | Benning |
| 2,597,702 A | 5/1952 | Benning |
| 2,599,140 A | 6/1952 | Taub |
| 2,855,367 A | 10/1958 | Buck |
| 3,131,153 A | 4/1964 | Klausner |
| 3,395,214 A | 7/1968 | Mummert |
| 3,708,435 A | 1/1973 | Starkman |
| 3,709,437 A | 1/1973 | Wright |
| 3,770,648 A | 11/1973 | Mackles |
| 3,787,566 A | 1/1974 | Gauvreau et al. |
| 3,824,303 A | 7/1974 | Lanzet |
| 3,928,558 A | 12/1975 | Cheesman et al. |
| 3,962,150 A | 6/1976 | Viola |
| 3,963,507 A | 6/1976 | Kuramoto et al. |
| 4,018,364 A | 4/1977 | Wright |
| 4,086,178 A | 4/1978 | Walker |
| 4,220,665 A | 9/1980 | Klein |
| 4,311,695 A | 1/1982 | Starch |
| 4,313,978 A | 2/1982 | Stevens |
| 4,336,151 A | 6/1982 | Like et al. |
| 4,440,652 A | 4/1984 | Hunter |
| 4,440,653 A | 4/1984 | Briscoe |
| 4,454,060 A | 6/1984 | Lai et al. |
| 4,478,853 A | 10/1984 | Chaussee |
| 4,511,486 A | 4/1985 | Shah |
| 4,559,226 A | 12/1985 | Fogel et al. |
| 4,567,038 A | 1/1986 | Ciaudelli et al. |
| 4,584,189 A | 4/1986 | Leipold |
| 4,613,592 A | 9/1986 | Benzoni |
| 4,714,568 A | 12/1987 | Hurnik et al. |
| 4,772,592 A | 9/1988 | Benzoni |
| 4,826,828 A | 5/1989 | Wilmott et al. |
| 4,839,166 A | 6/1989 | Grollier et al. |
| 4,839,167 A | 6/1989 | Yamamoto et al. |
| 4,857,302 A | 8/1989 | Decker et al. |
| 4,897,262 A | 1/1990 | Nandagiri et al. |
| 4,906,459 A | 3/1990 | Cobb et al. |
| 4,915,934 A | 4/1990 | Tomlinson |
| 4,919,837 A | 4/1990 | Glack |
| 4,956,170 A | 9/1990 | Lee |
| 4,956,173 A | 9/1990 | Le Fur et al. |
| 4,981,678 A | 1/1991 | Tomlinson |
| 4,983,377 A | 1/1991 | Murphy et al. |
| 4,986,922 A | 1/1991 | Snow et al. |
| 4,988,453 A | 1/1991 | Chambers |
| 5,015,228 A | 5/1991 | Columbus et al. |
| 5,043,088 A | 8/1991 | Falla |
| 5,047,249 A | 9/1991 | Rothman et al. |
| 5,073,371 A | 12/1991 | Turner et al. |
| 5,100,658 A | 3/1992 | Bolich, Jr. et al. |
| 5,104,646 A | 4/1992 | Bolich, Jr. et al. |
| 5,122,541 A | 6/1992 | Eggensperger et al. |
| 5,128,123 A | 7/1992 | Brewster et al. |
| 5,167,950 A | 12/1992 | Lins |
| 5,180,584 A | 1/1993 | Sebag et al. |
| 5,204,099 A | 4/1993 | Barbier et al. |
| D338,585 S | 8/1993 | Bell |

(Continued)

FOREIGN PATENT DOCUMENTS

AU   2003203452   10/2004

(Continued)

OTHER PUBLICATIONS

U.S. Appl. No. 12/446,569, filed Apr. 21, 2009, Veeger, et al.

(Continued)

*Primary Examiner* — John Pak
*Assistant Examiner* — Nathan W Schlientz
(74) *Attorney, Agent, or Firm* — McAndrews, Held & Malloy, Ltd.

(57) ABSTRACT

An alcoholic foam composition, which can be dispensed as a foam via a pump-foam system contains a) at least 52 to ≦99 wt % of an alcohol or mixture of alcohols, b) a surfactant or a surfactant mixture, c) at least one polyalkylene glycol, d) optionally, at least one foam stabilizer, e) optionally, at least one member selected from the group consisting of cosmetic auxiliaries, adjuvants, active ingredients, and mixtures thereof, and f) optionally water. The surface tension of component b) lies in the range of ±15 dyn/cm of the surface tension of component a) or corresponds to the surface tension of component a), and the sum of components a) to f) is 100 wt % relative to the total quantity of the foam composition.

21 Claims, No Drawings

U.S. PATENT DOCUMENTS

| | | | |
|---|---|---|---|
| 5,232,691 A | 8/1993 | Lemole | |
| 5,256,401 A | 10/1993 | Duckenfield | |
| 5,265,772 A | 11/1993 | Bartasevich | |
| 5,266,598 A | 11/1993 | Ninomiya et al. | |
| D343,751 S | 2/1994 | Bell | |
| 5,288,486 A | 2/1994 | White | |
| 5,290,555 A | 3/1994 | Guthauser et al. | |
| D346,332 S | 4/1994 | Kanfer | |
| 5,300,284 A | 4/1994 | Wiechers et al. | |
| 5,314,684 A | 5/1994 | Horoschak et al. | |
| 5,336,497 A | 8/1994 | Guerrero et al. | |
| 5,352,437 A | 10/1994 | Nakagawa et al. | |
| 5,362,484 A | 11/1994 | Wood et al. | |
| 5,370,267 A | 12/1994 | Schroeder | |
| 5,415,811 A | 5/1995 | Wile | |
| 5,441,178 A | 8/1995 | Wysocki | |
| 5,443,236 A | 8/1995 | Bell | |
| 5,445,288 A | 8/1995 | Banks | |
| 5,449,137 A | 9/1995 | Bell | |
| 5,462,688 A | 10/1995 | Lippman | |
| D365,509 S | 12/1995 | Bell | |
| D365,518 S | 12/1995 | Wysocki | |
| D365,755 S | 1/1996 | Kanfer | |
| 5,484,597 A | 1/1996 | Slavtcheff et al. | |
| 5,494,533 A | 2/1996 | Woodin, Jr. et al. | |
| 5,523,014 A | 6/1996 | Dolan | |
| 5,547,662 A | 8/1996 | Khan et al. | |
| 5,549,888 A | 8/1996 | Venkateswaran | |
| 5,558,453 A | 9/1996 | Bell | |
| 5,567,428 A | 10/1996 | Hughes | |
| 5,587,358 A | 12/1996 | Sukigara | |
| 5,607,980 A | 3/1997 | McAfee et al. | |
| 5,612,324 A | 3/1997 | Guang Lin et al. | |
| 5,625,659 A | 4/1997 | Sears | |
| 5,626,853 A | 5/1997 | Bara et al. | |
| 5,629,006 A | 5/1997 | Hoang | |
| 5,635,462 A | 6/1997 | Fendler | |
| 5,635,469 A | 6/1997 | Fowler et al. | |
| D383,001 S | 9/1997 | Bell | |
| 5,662,893 A | 9/1997 | George et al. | |
| 5,665,332 A | 9/1997 | Mundschenk et al. | |
| D385,795 S | 11/1997 | Wysocki | |
| 5,690,921 A | 11/1997 | Lang et al. | |
| 5,693,255 A | 12/1997 | Okamoto et al. | |
| 5,718,353 A | 2/1998 | Kanfer | |
| 5,719,113 A | 2/1998 | Fendler | |
| D392,136 S | 3/1998 | Ross | |
| 5,725,131 A | 3/1998 | Bell et al. | |
| 5,733,535 A | 3/1998 | Hollingshead et al. | |
| 5,756,077 A | 5/1998 | Syed et al. | |
| 5,767,161 A | 6/1998 | Stroppolo et al. | |
| 5,776,430 A | 7/1998 | Osborne et al. | |
| 5,789,371 A | 8/1998 | Tracy et al. | |
| 5,824,320 A | 10/1998 | Rouillard et al. | |
| D400,799 S | 11/1998 | Bell | |
| 5,834,516 A | 11/1998 | O'Lenick, Jr. | |
| 5,856,347 A | 1/1999 | Hashiguchi et al. | |
| 5,863,884 A | 1/1999 | Lafreniere | |
| 5,902,778 A | 5/1999 | Hartmann et al. | |
| 5,906,808 A | 5/1999 | Osborne | |
| D411,456 S | 6/1999 | Mast | |
| 5,908,619 A | 6/1999 | Scholz | |
| 5,919,439 A | 7/1999 | Torgerson et al. | |
| 5,922,663 A | 7/1999 | Gabriel et al. | |
| 5,928,993 A | 7/1999 | Johansson | |
| 5,935,587 A | 8/1999 | Cauwet et al. | |
| 5,944,227 A | 8/1999 | Schroeder | |
| 5,951,993 A | 9/1999 | Scholz | |
| 5,952,290 A | 9/1999 | Li et al. | |
| 5,955,408 A | 9/1999 | Kaiser | |
| 5,955,416 A | 9/1999 | Baillely et al. | |
| D415,343 S | 10/1999 | Maddox | |
| 5,972,356 A | 10/1999 | Peffly et al. | |
| D416,417 S | 11/1999 | Ross | |
| 5,980,876 A | 11/1999 | Peffy | |
| 5,996,851 A | 12/1999 | Dolan | |
| D418,708 S | 1/2000 | Kanfer | |
| 6,019,997 A | 2/2000 | Scholz et al. | |
| 6,022,551 A | 2/2000 | Jampani et al. | |
| 6,039,965 A | 3/2000 | Donian et al. | |
| D422,828 S | 4/2000 | Kanfer | |
| 6,065,639 A | 5/2000 | Maddox | |
| 6,086,856 A | 7/2000 | Saferstein et al. | |
| 6,090,395 A | 7/2000 | Asmus | |
| 6,117,440 A | 9/2000 | Suh | |
| 6,130,253 A | 10/2000 | Franklin et al. | |
| 6,183,766 B1 | 2/2001 | Sine et al. | |
| 6,217,885 B1 | 4/2001 | Roder et al. | |
| 6,255,265 B1 | 7/2001 | Van Gunst | |
| 6,262,128 B1 | 7/2001 | Stern et al. | |
| 6,265,363 B1 | 7/2001 | Viscovitz | |
| 6,267,946 B1 | 7/2001 | Barnhart | |
| 6,274,124 B1 | 8/2001 | Vollhardt | |
| 6,277,359 B1 | 8/2001 | Raths et al. | |
| 6,319,958 B1 | 11/2001 | Johnson et al. | |
| 6,333,039 B1 | 12/2001 | Fendler et al. | |
| 6,339,165 B1 | 1/2002 | Endo et al. | |
| 6,342,470 B1 | 1/2002 | Aronson | |
| 6,352,701 B1 | 3/2002 | Scholz et al. | |
| 6,358,914 B1 | 3/2002 | Gabriel et al. | |
| 6,376,438 B1 | 4/2002 | Rosenberger et al. | |
| 6,383,505 B1 | 5/2002 | Kaiser | |
| 6,383,997 B1 | 5/2002 | McManus | |
| 6,410,005 B1 | 6/2002 | Galleguillos et al. | |
| 6,423,329 B1 | 7/2002 | Sine et al. | |
| 6,462,002 B2 | 10/2002 | Saxena | |
| 6,471,983 B1 | 10/2002 | Veeger et al. | |
| 6,472,356 B2 | 10/2002 | Narula et al. | |
| 6,479,442 B1 | 11/2002 | Berube | |
| 6,489,275 B1 | 12/2002 | Veeger et al. | |
| 6,491,840 B1 | 12/2002 | Frankenbach et al. | |
| 6,497,864 B1 | 12/2002 | Samain et al. | |
| 6,518,228 B1 | 2/2003 | Jorgensen | |
| 6,524,494 B2 | 2/2003 | Hart et al. | |
| 6,524,594 B1 | 2/2003 | Santora | |
| 6,528,544 B2 | 3/2003 | Stern et al. | |
| 6,534,069 B1 | 3/2003 | Asmus et al. | |
| 6,537,952 B2 | 3/2003 | Hayward | |
| 6,551,605 B2 | 4/2003 | Bondo | |
| 6,555,508 B1 | 4/2003 | Paul et al. | |
| 6,562,360 B2 | 5/2003 | Scholz | |
| 6,585,711 B1 | 7/2003 | Asmus et al. | |
| 6,592,880 B1 | 7/2003 | Jager | |
| 6,610,315 B2 | 8/2003 | Scholz | |
| 6,617,294 B2 | 9/2003 | Narula et al. | |
| 6,623,744 B2 | 9/2003 | Asmus | |
| 6,638,527 B2 | 10/2003 | Gott | |
| 6,641,825 B2 | 11/2003 | Scholz | |
| 6,664,256 B1 | 12/2003 | Oohkuchietal | |
| 6,664,356 B1 | 12/2003 | Shih | |
| 6,666,217 B2 | 12/2003 | Elsner | |
| 6,685,952 B1 | 2/2004 | Ma et al. | |
| 6,689,593 B2 | 2/2004 | Millis | |
| 6,696,397 B2 | 2/2004 | Staats | |
| 6,703,007 B2 | 3/2004 | Glenn, Jr. | |
| 6,706,675 B1 | 3/2004 | Demson | |
| 6,709,647 B2 | 3/2004 | Bhakoo | |
| 6,710,022 B1 | 3/2004 | Kwetkat et al. | |
| 6,723,689 B1 | 4/2004 | Hoang | |
| 6,730,621 B2 | 5/2004 | Gott | |
| 6,759,376 B2 | 7/2004 | Zhang | |
| 6,762,158 B2 | 7/2004 | Lukenbach | |
| 6,777,384 B2 | 8/2004 | Raths et al. | |
| 6,780,826 B2 | 8/2004 | Zhang | |
| 6,794,345 B2 | 9/2004 | Elsner et al. | |
| 6,797,687 B2 | 9/2004 | Kischket et al. | |
| 6,805,141 B2 | 10/2004 | Elsner et al. | |
| 6,815,410 B2 | 11/2004 | Boutique | |
| 6,818,603 B2 | 11/2004 | Aleles | |
| 6,846,846 B2 | 1/2005 | Modak et al. | |
| 6,875,539 B2 | 4/2005 | Ophardt | |
| 6,884,763 B2 | 4/2005 | Willard | |
| 6,946,120 B2 | 9/2005 | Wai-Chiu et al. | |
| 6,977,082 B2 | 12/2005 | Seitz, Jr. et al. | |
| 7,081,246 B2 | 7/2006 | Asmus et al. | |
| 7,141,237 B2 | 11/2006 | Abram et al. | |
| 7,163,916 B2 | 1/2007 | Allef et al. | |

| | | |
|---|---|---|
| 7,164,041 B1 | 1/2007 | Moore et al. |
| 7,166,435 B2 | 1/2007 | Rosenbloom |
| 7,199,090 B2 | 4/2007 | Koivisto |
| 7,241,452 B2 | 7/2007 | Veeger et al. |
| 7,297,675 B2 | 11/2007 | Allef et al. |
| 7,393,817 B2 | 7/2008 | Kwetkat et al. |
| 7,530,477 B2 | 5/2009 | Ophardt |
| 7,547,732 B2 | 6/2009 | Moore et al. |
| 7,566,460 B2 | 7/2009 | Asmus |
| 7,651,990 B2 | 1/2010 | Asmus |
| 7,670,615 B2 | 3/2010 | Veeger et al. |
| 7,683,018 B2 | 3/2010 | Koivisto et al. |
| 7,723,279 B2 | 5/2010 | Lestage et al. |
| 7,790,663 B2 | 9/2010 | Lestage et al. |
| 7,803,390 B2 | 9/2010 | Asmus et al. |
| 7,842,725 B2 | 11/2010 | Wegner et al. |
| 8,058,315 B2 | 11/2011 | Wegner et al. |
| 2002/0022660 A1 | 2/2002 | Jampani |
| 2002/0028187 A1 | 3/2002 | Nekludoff et al. |
| 2002/0039562 A1 | 4/2002 | Kobayashi et al. |
| 2002/0098159 A1 | 7/2002 | Wei et al. |
| 2002/0108640 A1 | 8/2002 | Barger et al. |
| 2002/0127253 A1 | 9/2002 | Scholz et al. |
| 2002/0142018 A1 | 10/2002 | Scholz et al. |
| 2002/0151446 A1 | 10/2002 | Piterski et al. |
| 2002/0160029 A1 | 10/2002 | Asmus et al. |
| 2002/0160924 A1 | 10/2002 | Bertrem et al. |
| 2002/0177535 A1 | 11/2002 | Piterski et al. |
| 2002/0187908 A1 | 12/2002 | Gagilardi et al. |
| 2003/0134761 A1 | 7/2003 | Sebillotte-Arnaud et al. |
| 2003/0203824 A1 | 10/2003 | Staats |
| 2003/0211066 A1 | 11/2003 | Scholz et al. |
| 2003/0213542 A1 | 11/2003 | Kobayashi et al. |
| 2003/0215418 A1 | 11/2003 | Asmus et al. |
| 2003/0235550 A1 | 12/2003 | Pan et al. |
| 2004/0001797 A1 | 1/2004 | Saud et al. |
| 2004/0071748 A1 | 4/2004 | Asmus et al. |
| 2004/0072700 A1 | 4/2004 | Gupta |
| 2004/0102429 A1 | 5/2004 | Modak |
| 2004/0170592 A1 | 9/2004 | Veeger et al. |
| 2004/0191195 A1 | 9/2004 | Collins et al. |
| 2004/0191274 A1 | 9/2004 | Grayson et al. |
| 2004/0219227 A1 | 11/2004 | Modak et al. |
| 2004/0241099 A1 | 12/2004 | Popp et al. |
| 2004/0247685 A1 | 12/2004 | Modak et al. |
| 2004/0265240 A1 | 12/2004 | Tamarkin et al. |
| 2005/0003990 A1 | 1/2005 | Smith et al. |
| 2005/0031580 A1 | 2/2005 | Allef et al. |
| 2005/0031653 A1 | 2/2005 | Kwetkat et al. |
| 2005/0063925 A1 | 3/2005 | Candau et al. |
| 2005/0109981 A1 | 5/2005 | Tucker et al. |
| 2005/0129626 A1 | 6/2005 | Koivisto et al. |
| 2005/0152931 A1 | 7/2005 | SaNogueira et al. |
| 2005/0222001 A1 | 10/2005 | Baumeister et al. |
| 2005/0226838 A1 | 10/2005 | Krause et al. |
| 2005/0277574 A1 | 12/2005 | Niedbala et al. |
| 2006/0018847 A1 | 1/2006 | Kroepke et al. |
| 2006/0104911 A1 | 5/2006 | Novak |
| 2006/0104919 A1 | 5/2006 | Novak |
| 2006/0110416 A1 | 5/2006 | Ryles et al. |
| 2006/0121071 A1 | 6/2006 | Asmus |
| 2006/0165627 A1 | 7/2006 | Allef et al. |
| 2006/0182690 A1 | 8/2006 | Veeger |
| 2006/0198859 A1 | 9/2006 | Allef et al. |
| 2006/0204468 A1 | 9/2006 | Allef et al. |
| 2006/0257334 A1 | 11/2006 | Dahms et al. |
| 2006/0263396 A1 | 11/2006 | Asmus |
| 2006/0275226 A1 | 12/2006 | Dahms et al. |
| 2006/0281663 A1 | 12/2006 | Asmus |
| 2007/0027055 A1 | 2/2007 | Koivisto et al. |
| 2007/0041927 A1 | 2/2007 | Blaeser et al. |
| 2007/0065383 A1 | 3/2007 | Fernandez de Castro et al. |
| 2007/0092470 A1 | 4/2007 | Allef et al. |
| 2007/0141007 A1 | 6/2007 | Glynn et al. |
| 2007/0148101 A1 | 6/2007 | Snyder et al. |
| 2007/0179207 A1 | 8/2007 | Fernandez de Castro et al. |
| 2007/0258911 A1 | 11/2007 | Fernandez de Castro et al. |
| 2008/0051312 A1 | 2/2008 | Lestage et al. |
| 2008/0108704 A1 | 5/2008 | Asmus et al. |
| 2008/0145320 A1 | 6/2008 | Wenk et al. |
| 2008/0207767 A1 | 8/2008 | Dobos |
| 2008/0293825 A1 | 11/2008 | Littau et al. |
| 2008/0305056 A1 | 12/2008 | Jenni et al. |
| 2009/0054521 A1 | 2/2009 | Herrwerth et al. |
| 2009/0098067 A1 | 4/2009 | Seidling et al. |
| 2009/0318570 A1 | 12/2009 | Veeger et al. |
| 2009/0326076 A1 | 12/2009 | Asmus |
| 2010/0022660 A1 | 1/2010 | Wegner et al. |
| 2010/0160415 A1 | 6/2010 | Koivisto et al. |
| 2010/0187263 A1 | 7/2010 | Lestage et al. |
| 2010/0210499 A1 | 8/2010 | Allef et al. |
| 2010/0234475 A1 | 9/2010 | Wegner et al. |
| 2010/0327013 A1 | 12/2010 | Asmus |
| 2010/0331411 A1 | 12/2010 | Asmus |
| 2011/0104079 A1 | 5/2011 | Snyder et al. |
| 2011/0110869 A1 | 5/2011 | Scholz et al. |

FOREIGN PATENT DOCUMENTS

| | | |
|---|---|---|
| CA | 2 323 780 A1 | 4/2001 |
| CA | 2534692 | 2/2005 |
| CA | 2587086 | 8/2005 |
| CA | 2 587 086 A1 | 4/2006 |
| DE | 28 52 593 C2 | 6/1979 |
| DE | 3306593 A1 | 2/1983 |
| DE | 33 06 593 A1 | 9/1983 |
| DE | 19523320 | 1/1997 |
| DE | 695 12 841 T2 | 5/2000 |
| DE | 696 30 221 T2 | 7/2004 |
| DE | 69512841 | 5/2005 |
| DE | 10 2004 050 211 | 4/2006 |
| EP | 0160051 | 10/1984 |
| EP | 0 160 051 B1 | 11/1985 |
| EP | 0213527 | 3/1987 |
| EP | 0117889 | 11/1987 |
| EP | 0 260 641 | 3/1988 |
| EP | 0384126 | 1/1990 |
| EP | 0 384 126 | 8/1990 |
| EP | 0 689-767 A2 | 1/1996 |
| EP | 0689767 | 1/1996 |
| EP | 0882446 | 12/1998 |
| EP | 0990412 | 4/2000 |
| EP | 1118655 | 7/2001 |
| EP | 1 584 323 A1 | 10/2005 |
| EP | 1584323 | 10/2005 |
| EP | 1 893 197 | 3/2008 |
| EP | 1967576 A1 | 9/2008 |
| EP | 1811013 | 8/2009 |
| GB | 1 010 874 A | 7/1979 |
| GB | 2010874 | 7/1979 |
| JP | 11349418 | 12/1999 |
| JP | 07285808 A | 11/2007 |
| WO | 9307250 | 10/1991 |
| WO | 9300089 | 1/1993 |
| WO | WO 93/07250 | 4/1993 |
| WO | 95/01384 | 1/1995 |
| WO | 95/03772 | 2/1995 |
| WO | 97/00667 | 1/1997 |
| WO | 97/00667 A1 | 1/1997 |
| WO | 9700668 | 1/1997 |
| WO | WO 97/00668 | 1/1997 |
| WO | 9920250 | 4/1999 |
| WO | 0006107 | 2/2000 |
| WO | 0047183 | 8/2000 |
| WO | 02062936 | 8/2002 |
| WO | 03028671 | 9/2002 |
| WO | WO 03/028671 A2 | 4/2003 |
| WO | 03034994 | 5/2003 |
| WO | 03053388 | 7/2003 |
| WO | 2004000016 | 12/2003 |
| WO | 2005030917 | 9/2004 |
| WO | 05030917 | 4/2005 |
| WO | 2005051341 | 6/2005 |
| WO | 2005123012 | 6/2005 |
| WO | 2005/123012 A1 | 12/2005 |
| WO | 2006/042588 A1 | 4/2006 |
| WO | 2006042588 | 4/2006 |
| WO | 2006066888 | 6/2006 |
| WO | 2006094387 | 9/2006 |

| | | |
|---|---|---|
| WO | 2006138111 | 12/2006 |
| WO | 2007095008 | 8/2007 |
| WO | 2008132621 | 11/2008 |
| WO | 2010010475 | 1/2010 |

OTHER PUBLICATIONS

U.S. Appl. No. 12/674,831, filed Feb. 23, 2010, Wenk, et al.
U.S. Appl. No. 12/863,868, filed Jul. 21, 2010, Allef, et al.
U.S. Appl. No. 12/933,835, filed Sep. 21, 2010, Allef, et al.
Degusszi: Goldschmidt Personal Care, Catalogue of Products, p. 30, Oct. 2004.
S. C. Cnema, et al., "Foaming of Anhydrous Methanol for Well Stimulation", Society of Petroleum Engineers, SPE 13565, (1985).
Paul A. Sanders, "Aqueous Alcohol Aerosol Foams", Drug & Cosmetic Industry, XP000960450, vol. 99, No. 2, 1966, pp. 56, 58, 60, 142, 143, 146-154.
Patent Abstracts of Japan—English Abstract of 07285808 A (application No. 05343940, filed Dec. 18, 1993).
Patent Abstracts of Japan—English Abstract of 06279268 A (application No. 06022166, filed Jan. 21, 1994).
Patent Abstracts of Japan—English Abstract of 113494118 A (application No. 10159268, filed Jun. 8, 1998).
Office Action from the Chinese Patent Office (translation) dated Aug. 25, 2010 for Application No. 200680015637.1.
Response to Canadian Patent Office dated May 26, 2010 for Application No. 2,540,085.
Amendments submitted to EPO dated May 26, 2010 for Application No. 06705273.8.
Response to the Australian Patent Office dated Mar. 23, 2010 for Application No. 2004275900.
Response to the Canadian Patent Office dated Mar. 18, 2010 for Application No. 2,595,025.
Amendment filed with the New Zealand Patent Office dated Dec. 21, 2009 for Application No. 561741.
Response to the Canadian Patent Office dated Dec. 22, 2009 for Application No. 2,540,085.
Response to the New Zealand Patent Office dated Nov. 19, 2009 for Application No. 561741.
Response to Canadian Patent Office dated Nov. 10, 2009 for Application No. 2,595,025.
Office Action from the Ukranian Patent Office (translation) dated Jul. 30, 2009 for Application No. a 200710192/M.
Office Action dated May 10, 2011 in U.S. Appl. No. 12/878,786.
Office Action dated May 10, 2011 in U.S. Appl. No. 12/878,793.
Office Action dated Apr. 29, 2011 in U.S. Appl. No. 12/552,126.
Reply from Australian Patent Office dated Jun. 1, 2010 for Application No. 2005318384.
Communication dated Mar. 9, 2011 in the opposition to European Patent 1 811 013.
Amendment dated Feb. 23, 2011 in U.S. Appl. No. 12/179,410.
Amendment and Response dated Feb. 18, 2011 in U.S. Appl. No. 12/878,786.
Amendment and Response dated Feb. 18, 2011 in U.S. Appl. No. 12/878,793.
Amendment and Response dated Feb. 18, 2011 in U.S. Appl. No. 12/552,126.
Office Action dated May 24, 2011 in U.S. Appl. No. 12/179,410.
Office Action dated Feb. 15, 2011 in U.S. Appl. No. 11/806,767.
Request for Certificate of Correction for US Patent No. 7,651,990 (U.S. Appl. No. 11/151,563) mailed Jun. 20, 2011.
Communication dated Jun. 20, 2011 in European Application No. 06 772 279.3.
Communication dated Apr. 26, 2010 in European Application No. 04786634.8.
Response to Office Action and Amendments dated Oct. 7, 2010 for Canadian Application No. 2,595,025.
Communication dated Jan. 1, 2010 in European Application No. 04786634.8.
Office Action dated May 26, 2011 in U.S. Appl. No. 12/659,063.
Appellant's Brief on Appeal dated Jun. 13, 2011 in U.S. Appl. No. 11/075,287.
Appellant's Brief on Appeal dated Jun. 14, 2011 in U.S. Appl. No. 11/369,381.

EP 1 233 749 issued Nov. 21, 2011, Biering, Holger (English-language claims).
Brochure, Polyox Water-Soluble Resins, Nordmann, Rassmann GmbH, Hamburg, Germany, Dec. 16, 2004 or earlier.
DE 10 2004 062 775 A1 filed on Dec. 21, 2004 (Certified translation).
The Dow Chemical Company Sales Specification for Specified Material 00029789-S: Ethocel Standard 100 Industrial Ethylcellulose printed Sep. 11, 2001.
The Dow Chemical Company Sales Specification for Specified Material 00116267-S: Ethocel Standard 300 Industrial Ethylcellulose printed Sep. 11, 2001.
The Dow Chemical Company Sales Specification for Specified Material 00129064-S: Polyox ™ WSR N10 Amerchol printed Feb. 28, 2003.
The Dow Chemical Company Sales Specification for Specified Material 00129042-S: Polyox ™ WSR N3000 Amerchol printed Feb. 18, 2003.
The Dow Chemical Company Sales Specification for Specified Material 00126141-S: Polyox™ WSR N60K printed Feb. 18, 2003.
Toxicological Test Results From Literature, Final Report of the Safety Assigment of Dimethicone Copolyol, Journal of American College of Toxicology, vol. 1, No. 4, 1982 dated Jul. 30, 2001 (Goldschmidt Personal Care—Degussa).
Floyd, et al., "Performance-Drive: New Silicone Copolymers," Global Cosmetics Industry, Sep. 2000.
Degussa Creating Essentials, Product Data Record for ABIL® B 8832 (3 pages) dated Jul. 14, 2004, Mat. No. 202534, Edition 1.
Degussa, Product Specification for ABIL® B 8832 (1 page) dated Aug. 26, 2004 (printed Sep. 6, 2004), Spec. No. ST-980121.
Degussa, Summary of toxicological and ecotoxicological data for ABIL® B 8832 (3 pages) dated May 17, 2002.
Dow PowerPoint Presentation entitled: "METHOCEL Applications in Personal Cleansing, a Superior Sensory Experience", Dec. 9, 2004 or earlier.
Dow PowerPoint Presentation entitled: ETHOCEL General Properties (15 pages, Dec. 9, 2004 or earlier).
Response to the Chinese Patent Office dated May 18, 2011 in Application No. 200680015637.1.
Deb Worldwide Healthcare Inc. and Deb Canadian Hygiene Inc., Plaintiffs, and Ecolab Co., Defendant, Court File No. T-379-11, Deb's Statement of Claim dated Mar. 7, 2011.
Deb Worldwide Healthcare Inc. and Deb Canadian Hygiene Inc., Plaintiffs, and Ecolab Co., Defendant, Court File No. T-379-11, Ecolab's Statement of Defense and Counterclaim dated Jun. 3, 2011.
Deb Worldwide Healthcare Inc. and Deb Canadian Hygiene Inc., Plaintiffs, and Ecolab Co., Defendant, Court File No. T-379-11, Deb's Reply and Defence to Counterclaim dated Jul. 11, 2011.
Deb Worldwide Healthcare Inc. and Deb Canadian Hygiene Inc., Plaintiffs, and Ecolab Co., Defendant, Court File No. T-379-11, Ecolab's Reply to Defence to Counter dated Jul. 11, 2011.
Deb Worldwide Healthcare Inc., Applicants and Kimberly-Clark Australia Pty. Ltd., No. VID 294 of 2011, Statement of Cross-Claim dated Aug. 2, 2011 (Federal Court of Australia, District Victoria, General Division).
Deb Worldwide Healthcare Inc., Applicants and Kimberly-Clark Australia Pty. Ltd., No. VID 294 of 2011, Notice of Filing, Statement of Claim and Certificate of Legal Representation dated Apr. 18, 2011 (Federal Court of Australia, District Victoria, General Division).
Amendment in U.S. Appl. No. 12/787,624 filed on Jul. 19, 2011.
Notice of Allowance in U.S. Appl. No. 12/787,624 mailed on Aug. 5, 2011.
Communication in European Application No. 06 772 279.3-2108 dated Jun. 20, 2011.
Office Action dated May 13, 2011 in U.S. Appl. No. 12/787,624.
Office Action dated Apr. 15, 2011 in U.S. Appl. No. 10/591,243.
Office Action dated Apr. 11, 2011 in U.S. Appl. No. 11/806,767.
Acknowledgement of documents and Summons to Attend Oral Proceedings dated Sep. 9, 2011 for EP Patent No. 18110130.
U.S. Office Action mailed Jun. 28, 2010 for U.S. Appl. No. 11/438,664.
Preliminary Amendment dated Jul. 24, 2008 in U.S. Appl. No. 12/179,410 (Publication No. 2008-0293825 published on Nov. 27, 2008).

International Search Report for International Application No. PCT/US2006/021904 mailed Oct. 24, 2006.
Notice of Allowance dated Jul. 20, 2010 for U.S. Appl. No. 12/179,382.
Supplemental Response and Amendment filed on Aug. 13, 2010 for U.S. Appl. No. 12/032,083.
Request for Continued Examination filed on Jul. 6, 2010 for U.S. Appl. No. 12/032,083.
Advisory Action Communication mailed Jun. 29, 2010 for U.S. Appl. No. 12/032,083.
U.S. Office Action mailed Aug. 3, 2010 for U.S. Appl. No. 11/075,287.
U.S. Office Action mailed Aug. 3, 2010 for U.S. Appl. No. 11/369,381.
Response and Amendment after Final Office Action filed on Jun. 2, 2010 for U.S. Appl. No. 12/032,083.
Communication of Notices of Opposition to a European Patent (EP 1 811 013) filed by Ecolab, Inc., 3M Innovative Properties Company and DEB Worldwide Healthcare Inc. against Gojo Industries dated Jun. 16, 2010.
Affidavit of Bruce Michael Koivisto signed and dated on May 17, 2010.
"Dow Corning@ 190 Fluid" product information. Dow Corning, Midland, MI Feb. 24, 2010, Ref. No. 22-1616E-01 (3 pages).
Printout of http://www.rexamairspray.com/products-foampump.php Oct. 5, 2010 (2 pages).
Notice of Opposition to a European Patent (EP 1 811 013) filed by 3M Innovative Properties Company against Gojo Industries dated May 12, 2010.
Notice of Opposition to a European Patent (EP 1 811 013) filed by Ecolab, Inc. against Gojo Industries dated May 6, 2010.
Affidavit of Caroline Fellows dated May 10, 2010.
Technical Information for Luviquat® PQ 11, BASF, May 1997 (3 pages).
Response and Amendment dated Apr. 7, 2010 for U.S. Appl. No. 11/438,664.
Declaration of Amanda J. Copeland dated Apr. 7, 2010.
Notice of Opposition to a European Patent (EP 1 811 013) filed by DEB Worldwide Healthcare Inc. against Gojo Industries dated May 12, 2010.
Complaint for Correction of Inventorship of Patent; Case 1:10-CV-00266-GMS, filed Apr. 2, 2010 in the United States District Court for the District of Delaware.
Worldwide Healthcare, Inc., "Material Safety Data Sheet", Jan. 24, 2007.
Office Action mailed Mar. 16, 2009 in U.S. Appl. No. 11/312,559.
U.S. Office Action mailed Jun. 24, 2010 for U.S. Appl. No. 12/659,063.
Amendment and Response filed Jul. 3, 2006 in U.S. Appl. No. 10/992,494.
Non-Final Rejection mailed Sep. 26, 2006 in U.S. Appl. No. 10/992,494.
Amendment and Response and RCE filed Mar. 26, 2007 in U.S. Appl. No. 10/992,494.
Non-Final Rejection mailed Apr. 9, 2007 in U.S. Appl. No. 10/992,494.
Final Rejection mailed May 7, 2007 in U.S. Appl. No. 11/048,031.
Non-Final Rejection mailed May 11, 2006 in U.S. Appl. No. 11/048,031.
Amendment and Response filed Aug. 11, 2006 in U.S. Appl. No. 11/048,031.
Final Rejection mailed Feb. 11, 2008 in U.S. Appl. No. 11/048,040.
Amendment and Response filed Nov. 29, 2007 in U.S. Appl. No. 11/048,040.
Notice of Non-Compliant Amendment mailed Oct. 29, 2007 in U.S. Appl. No. 11/048,040.
Amendment and Response filed Oct. 16, 2007 in U.S. Appl. No. 11/048,040.
Non-Final Rejection mailed Jul. 16, 2007 in U.S. Appl. No. 11/048,040.
Amendment and Response filed Jun. 11, 2007 in U.S. Appl. No. 11/048,040.
Notice of Non-Complaint Amendment mailed Jun. 1, 2007 in U.S. Appl. No. 11/048,040.
Amendment and Response and RCE filed May 21, 2007 in U.S. Appl. No. 11/048,040.
Final Rejection mailed Nov. 20, 2006 in U.S. Appl. No. 11/1048,040.
Amendment and Response filed Sep. 5, 2006 in U.S. Appl. No. 11/048,040.
Non-Final Rejection mailed Jul. 18, 2006 in U.S. Appl. No. 11/048,040.
Final Rejection mailed Jul. 9, 2008 in U.S. Appl. No. 11/151,563.
Office Action mailed Jul. 8, 2009 in U.S. Appl. No. 11/507,626.
Office Action mailed Mar. 19, 2009 in U.S. Appl. No. 11/507,626.
Office Action mailed Oct. 3, 2008 in U.S. Appl. No. 11/507,626.
Office Action mailed Oct. 21, 2008 in U.S. Appl. No. 11/151,563.
Office Action mailed Jul. 14, 2009 in U.S. Appl. No. 11/312,559.
Notice of Acceptance, U.S. Appl. No. 12/514,326, filed on May 11, 2009 and entitled "Composition, in Particular Cream to Protect Against Cold".
Interview Summary dated Jul. 14, 2009 for U.S. Appl. No. 11/312,559 filed on Dec. 21, 2005.
European Patent Specification EP 1 811 013 B1 published Aug. 12, 2009.
Request for Foreign Priority mailed Aug. 19, 2009 for U.S. Appl. No. 11/312,559 filed Dec. 21, 2005.
Request for RCE dated Sep. 1, 2009 in U.S. Appl. No. 11/151,563 filed Jun. 13, 2005.
Notice of Allowability dated Sep. 21, 2009 in U.S. Appl. No. 11/151,563 filed Jun. 13, 2005.
Non-Final Rejection mailed Sep. 17, 2009 for U.S. Appl. No. 12/032,083 filed Feb. 15, 2008.
Response dated Oct. 12, 2009 to European Patent Application No. 08250626.2.
Canadian Examination Report dated Oct. 13, 2009 in Application U.S. Appl. No. 2,595,025.
Notice of Allowability mailed Oct. 13, 2009 in U.S. Appl. No. 11/312,559 filed Dec. 21, 2005.
Office Action dated Oct. 15, 2009 in U.S. Appl. No. 11/438,664 filed May 22, 2006.
Examination Report dated Jul. 20, 2009 for New Zealand Patent Application No. 561741.
Complaint, *3M Company and 3M Innovative Properties Company* v. *Gojo Industries, Inc.*, United States District Court for the District of Minnesota. Case No. 0:10cv04065. Filed Sep. 28, 2010.
Rosen, Milton J., Dahanayake, Manilal, Industrial Utilization of Surfactants Principles and Practice. 2000.
Product Information 3M Flourad(TM).
Degussa, Creating Essentials, "Goldschmidt Personal Care", Catalogue of Products, May 2003.
Defendant BETCO, Corporation's Initial Disclosures Pursuant to Fed. R. Civ. P. 26(a)(1), *DEB Worldwide Healthcare, Inc.* v. *BETCO Corp.*, Case No. 3:08-cv-00052-bbc, US District Court for the Western District of Wisconsin.
First Amended Complaint, *DEB Worldwide Healthcare, Inc.* v. *BETCO Corp.*, Case No. 3:08-cv-00052-bbc, US District Court for the Western District of Wisconsin, document #21, Apr. 21, 2008.
Complaint, *DEB Worldwide Healthcare, Inc.* v. *BETCO Corp.*, Case No. 3:08-cv-00052-bbc, US District Court for the Western District of Wisconsin, document #1, Jan. 22, 2008.
Product Information Sheet, Mackanate DC-50, McIntyre Group Ltd., 1 page.
Product Information Sheet, Dow Corning 2501, Cosmetic Wax, 4 sheets.
Product Description, GE Silicones, SF1202, Dec. 22, 2004, 6 sheets.
Product Information, GE Silicones, SF 1388, Dec. 22, 2004, 2 sheets.
Product Information, DOW Corning, Sylgard 309 Silicone Surfactant, 3 sheets.
Product Description, GE Advance Materials Silicones, SF1388, 2 sheets Jan. 5, 2005.
Dewar et al., Effectiveness of Septisol Antiseptic Foam as a Surgical Scrub Agent, Applied Microbiology, Oct. 1973, vol. 26, No. 4, p. 544-549.
Beck, W., Alcohol foam for hand disinfection, AORN Journal, Dec. 1980, vol. 32, No. 6, p. 1087-1088.

3M Fluorad Well Stimulation Additive FC-742 Foamer for Aqueous/Alcoholic Fluids, 3M 1987, 6 pages.

Sandra J. Pfaff, Letters to the Editor, Alcohol Foam Use Questioned, AORN Journal, Dec. 1989, vol. 50, No. 6, 1 page.

3M Product Information Well Stimulation Additive FC-742, Foamer for Aqueous/Alcoholic Fluids, 1994, 4 pages.

Zonyl FSP fluorosurfactant, Techincal Information, DuPont, 1998, 2 pages.

Rosen et al., Industrial Utilization of Surfactants; Principles and Practice, AOCS Press, 2000, 4 pages.

Pabon et al., Fluorinated surfactants: synthesis, properties effluent treatment, J. Fluorine Chem. 114 (2002), p. 149-156.

Amendment and Response filed Oct. 31, 2007 in U.S. Appl. No. 11/340,778.

Amendment and Response filed Oct. 31, 2007 in U.S. Appl. No. 10/400,597.

Amendment and Request for Reconsideration filed Jun. 20, 2008 in U.S. Appl. No. 11/312,559.

Interview Summary mailed Apr. 23, 2008 in U.S. Appl. No. 11/312,559.

Non-Final Rejection mailed Feb. 20, 2008 in U.S. Appl. No. 11/312,559.

Amendment and Request for Reconsideration filed Jun. 22, 2007 in U.S. Appl. No. 11/312,559.

Non-Final Rejection mailed Feb. 22, 2007 in U.S. Appl. No. 11/312,559.

Amendment and Response filed Apr. 18, 2008 in U.S. Appl. No. 11/151,563.

Non-Final Rejection mailed Jan. 29, 2008 in U.S. Appl. No. 11/151,563.

Amendment and Response and RCE filed Nov. 13, 2007 in U.S. Appl. No. 11/151,563.

Advisory Action mailed Oct. 1, 2007 in U.S. Appl. No. 11/151,563.

Amendment and Response filed Sep. 11, 2007 in U.S. Appl. No. 11/151,563.

Final Rejection mailed Jun. 11, 2007 in U.S. Appl. No. 11/151,563.

Amendment and Response filed Mar. 19, 2007 in U.S. Appl. No. 11/151,563.

Non-Final Rejection mailed Oct. 19, 2006 in U.S. Appl. No. 11/151,563.

http://www.ipc.bas.bg/book1.htm (webpage regarding Exerowa et al., Foam and Foam Films; Theory, Experiment, Application, published by Elsevier (Dec. 1997)).

Final Rejection mailed Sep. 19, 2008 in U.S. Appl. No. 11/312,559.

Amendment and Response filed Jan. 2, 2006 in U.S. Appl. No. 10/992,494.

Response to Opposition (European Patent Application No. 06256249.1/European Patent No. EP 1 811 013) as filed by Ecolab, Inc. By Gojo Industries, Inc. dated Dec. 20, 2010.

U.S. Office Action mailed Jan. 19, 2011 for U.S. Appl. No. 11/075,287, filed Mar. 8, 2005.

U.S. Office Action mailed Jan. 19, 2011 for U.S. Appl. No. 11/369,381, filed Mar. 7, 2006.

Protest Under 37 C.F.R. 1.291 electronically filed on Dec. 20, 2010 for U.S. Appl. No. 12/878,786, filed Sep. 9, 2010.

U.S. Office Action mailed Dec. 13, 2010 for U.S. Appl. No. 12/878,786, filed Sep. 9, 2010.

Protest Under 37 C.F.R. 1.291 electronically filed on Dec. 20, 2010 for U.S. Appl. No. 12/878,793, filed Sep. 9, 2010.

U.S. Office Action mailed Dec. 10, 2010 for U.S. Appl. No. 12/878,793, filed Sep. 9, 2010.

U.S. Office Action mailed Dec. 13, 2010 for U.S. Appl. No. 12/552,126, filed Sep. 1, 2009.

Amendment electronically filed on Nov. 2, 2010 for U.S. Appl. No. 11/075,287, filed Mar. 8, 2005.

Response in European Patent Application No. 08250626.2 in the name of Gojo Industries, Inc. dated Oct. 12, 2009.

Supplemental Response and Amendment electronically filed on Aug. 13, 2010 for U.S. Appl. No. 12/032,083, filed Feb. 15, 2008.

U.S. Office Action mailed Aug. 3, 2010 for U.S. Appl. No. 11/075,287, filed Mar. 8, 2005.

U.S. Office Action mailed Aug. 3, 2010 for U.S. Appl. No. 11/369,381, filed Mar. 7, 2005.

Information Disclosure Statement electronically filed on Nov. 19, 2010 for U.S. Appl. No. 12/624,073, filed Nov. 23, 2009.

U.S. Office Action mailed Nov. 23, 2010 for U.S. Appl. No. 12/179,410, filed Jul. 24, 2008.

Office Action mailed Feb. 13, 2009 in U.S. Appl. No. 11/312,559.

Office Action mailed Dec. 4, 2008 in U.S. Appl. No. 11/312,559.

Notice of Allowance mailed Jun. 2, 2009 in U.S. Appl. No. 11/151,563.

Notice of Allowance and Fee(s) Due and Notice of Allowability mailed Nov. 24, 2009 for U.S. Appl. No. 11/151,563.

Interview Summary with Notification Date of Nov. 24, 2009 for U.S. Appl. No. 11/312,559.

Office Action for Canadian Patent Application No. 2,540,085 dated Oct. 29, 2008.

Examiner's first report for Australian Patent Application No. 2004 275900 dated May 21, 2009.

Wang, et al., "Direct Force Measurement of Comb Silicone Surfactants in Alcoholic Media by Atomic Force Microscopy", Journal of Colloid and Interface Science 242, 337-345 (2001).

Prieto et al., "Structure-function relationships of dimethicone copolyol", j. Cosmet. Sci., 51, 91-101 (Mar./Apr. 2000).

Japanese Patent Application No. 2008-500017, Drafting Date: May 26, 2011, Mailing Date: May 31, 2011 "Notice of Reasons for Rejection".

Japanese Publication No. 06-327750 published Nov. 29, 1994, "English Abstract of Reference 2".

Translation of Communication from the European Patent Office in Veeger et al, EP 05 825 981.3 (counterpart to U.S. Appl. No. 12/624,073).

Office Action dated Oct. 26, 2011 in U.S. Appl. No. 11/075,287, filed Mar. 8, 2005.

Appellant's Brief on Appeal dated Oct. 31, 2011 in U.S. Appl. No. 12/179,410, filed Jul. 24, 2008.

Office Communication from the US Patent Office dated Oct. 21, 2011 in U.S. Appl. No. 11/806,767, filed Jun. 4, 2007.

Office Communication from the US Patent Office dated Oct. 21, 2011 in U.S. Appl. No. 11/520,819, filed Sep. 14, 2006.

Translation of International Preliminary Report on Patentability from International Application No. PCT/EP2005/013742 dated Sep. 20, 2007.

US 7,754,762, 07/2010, Wegner et al. (withdrawn)

ALCOHOLIC PUMP FOAM

BACKGROUND OF THE INVENTION

1. Field of the Invention

The present invention relates to alcoholic foam compositions.

2. Discussion of the Background

Disinfectants are used to combat pathogenic microorganisms such as bacteria, viruses, spores, fungi, etc. The use of disinfectants is unavoidable in many regions or the use is expressly required by the legislators in many countries.

Disinfectants are usually classified according to their area of application and, depending on intended use, a distinction is made between antiseptics for wound, skin, stools and sputum disinfection as well as instruments disinfection, laundry and surface disinfectants, and especially also skin and hand disinfectants.

The area of application of the aforesaid disinfectants is medically indicated and they are used for prevention of infections in hospitals, doctors' and dentists' offices, in public areas such as schools, kindergartens, nursing institutions, retirement homes, sanatoriums, etc., and also in sports facilities and other places in which infections can be transmitted. Besides the use of disinfectants in the food industry and pharmaceutical industry, they are in general use not only at the workplace or in the home, but also in service industries such as laundries and kitchens, where the products are delivered directly to patients or consumers.

Demonstration of the effectiveness of such disinfecting agents for one or more of the aforesaid areas, of applications is achieved by thorough testing of these agents on the basis of standardized test methods, such as the guidelines of the German Association for Hygiene and Microbiology (DGHM) in Germany or the guidelines of the French Association for Standardization (AFNOR) in France. Examples of further standards are listed below:

| | |
|---|---|
| DIN EN 1040 | Chemical disinfectants and antiseptics (basic test) |
| DIN EN 1276 | Chemical disinfectants and antiseptics |
| | Bactericidal action in the fields of foods, industry, home and public institutions |
| DIN EN 1499 | Disinfecting hand washing |
| DIN EN 1500 | Hygienic hand disinfection |
| DIN EN 12054 | Chemical disinfectants and antiseptics |
| | Products for hygienic and surgical hand disinfection and hand washing - bactericidal effect |
| DIN EN 12791 | Surgical hand disinfectants |
| AFNOR T 72 300 | Bactericidal effectiveness of antiseptics and disinfectants that are employed as liquid mixed in water |
| AFNOR T 72 170 | Bactericidal effectiveness in the presence of interfering substances |
| NF EN 1040 | Bactericidal effectiveness of antiseptics and chemical disinfectants |
| NF EN 1275 | Fungicidal effectiveness of antiseptics and chemical disinfectants |

In the capacity of pharmaceuticals, antiseptics are further subject to legally governed approval and registration procedures.

For example, as can be seen from German Patent DE 4328828 A, various methods are available for achieving hand disinfection. Explicitly mentioned therein are the alcoholic hand disinfection methods that are standard in Germany as well as the scrub methods of hand disinfection. Products intended for hand disinfection among other purposes must satisfy at least the minimum requirements indicated in the aforesaid standards if they are to be certified as conforming with those standards and included as preparations in the disinfection list of the DGHM.

Commercially available disinfectants, especially skin and hand disinfectants, are usually composed of alcohol or mixtures of alcohols, optionally of active ingredients, which remain on the skin after evaporation of the alcohol components and which can be, for example, nonvolatile antimicrobial substances and/or common skin-care substances, and possibly other auxiliaries. If the alcohol component is used alone as the antimicrobial agent, the alcohol concentration in the product is to be chosen such that a disinfectant effect is assured even after evaporation of part of the alcohol. In this connection, it is known that this is the case for ethanolic compositions having an alcohol concentration of at least 52 wt %.

To address the disadvantages of alcoholic disinfectant solutions applied for skin and hand disinfection, thickeners have been added to such disinfectant solutions in order to increase the viscosity of these agents. Disadvantages include especially the difficulty of dosing due to the fact that the needed quantity of disinfectant often cannot be distributed uniformly over the skin or the hands and that aqueous alcohol solutions drip very easily from the hands. An example for added thickeners is found in European Patent EP 0604848 B, wherein the subject matter is a fast-drying disinfectant composition. As thickener there is described a combination of carboxyvinyl polymers and hydroxypropylmethylcellulose, wherein the total weight of the two components in the disinfectant composition is not greater than 3 wt %.

Also known are antimicrobial alcoholic gel compositions for skin and hand disinfection containing moisturizers and skin-care substances, as described in, for example, U.S. Pat. No. 4,956,170. In these compositions, cross-linked partly neutralized or neutralized acrylic acid polymers are used as thickeners. The antibacterial agent used in these compositions is 60 to 75 wt % of alcohol such as ethanol, isopropyl alcohol or mixtures thereof. Regarding the emollients contained in these gel compositions, especially petrolatum and other mineral-oil products that can be used in cosmetic preparations, as well as further hydrophobic constituents that can be used safely not only in cosmetics but also in disinfectants, it has been found that the use of such constituents in alcoholic gel compositions having high alcohol concentrations is highly detrimental to the stability of such gels, because the gels lose their viscosity and therefore their stability in the course of time during storage, and the compositions deliquesce. In general, it has been found that the gel stability suffers with increasing alcohol concentration, especially at alcohol concentrations higher than 60 wt %.

Such high alcohol concentrations, especially in gel compositions containing alcohol as the sole active component, are unavoidable, however, in order that such agents can also be certified as disinfectants for hand disinfection.

German Patent DE 10132382 discloses a simple, economic production method for the production of stable disinfectant hand-care and skin-care gels having high alcohol concentration, permitting the production of disinfectant hand-care gels that contain care components, that satisfy the standards

| DIN EN 1499 | Disinfecting hand washing |
| DIN EN 1500 | Hygienic hand disinfection | among others directly without further additional antimicrobial adjuvants, and that also have a hepatitis B activity. Although it has been shown that the application of a disinfectant agent in gel form is to be preferred to the application of a disinfectant agent in liquid form, especially as regards its drying-out tendency, such disinfectant alcoholic gel compositions nevertheless have the disadvantage that they must lose their gel structure upon being applied on the skin, in order to ensure uniform wetting of the skin areas and thus a safe disinfectant action.

Also known are alcoholic cleaning foam compositions, which are dispensed by commercially available pump-foam systems, which are to be found mainly in sanitary units of hospitals, doctors' and dentists' offices, schools, kindergartens and nursing institutions, such as old-age homes, sanatoriums, etc. The alcohol concentration of such foam compositions is only around 40 wt %, however, because the instability of the foams increases at higher alcohol concentrations. This can also be regarded as the reason why the advantageous form of application by means of foam, which is even more manageable than alcoholic gels, has not yet been considered for disinfectants, especially not for skin and hand disinfection, because of the low alcohol concentration of the products that have been commercially available heretofore.

SUMMARY OF THE INVENTION

It is an object of the present invention to provide an alcoholic foam composition that can be dispensed as pump foam, particularly via standard pump-foam systems, to the consumer for disinfection purposes, preferably for skin and hand disinfection.

It is another object of the present invention to provide an alcoholic foam that is stabilized in such a way that alcoholic foam having an alcohol concentration of at least 52 wt %, especially greater than 60 wt % of alcohol can be dispensed in order to ensure safe disinfection, especially skin and hand disinfection.

This and other objects have been achieved by the present invention the first embodiment of which includes an alcoholic foam composition, comprising:
  a) at least 52 to ≦99 wt %, relative to the total quantity of the foam composition, of an alcohol or mixture of alcohols,
  b) a surfactant or a surfactant mixture,
  c) at least one polyalkylene glycol,
  d) optionally, at least one foam stabilizer,
  e) optionally, at least one member selected from the group consisting of cosmetic auxiliaries, adjuvants, active ingredients, and mixtures thereof, and
  f) optionally water,
  wherein the surface tension of component b) lies in the range of ±15 dyn/cm of the surface tension of component a) or corresponds to the surface tension of component a), and wherein the sum of components a) to f) is 100 wt % relative to the total quantity of the foam composition.

DETAILED DESCRIPTION OF THE INVENTION

The present invention provides an alcoholic foam composition for disinfection, especially a pump-foam formulation, which contains the components
  a) at least 52 to ≦99 wt %, relative to the total quantity of the foam composition, of an alcohol or mixture of alcohols,
  b) a surfactant or a surfactant mixture,
  c) at least one polyalkylene glycol,
  d) optionally, at least one foam stabilizer,
  e) optionally, at least one member selected from the group consisting of cosmetic auxiliaries, adjuvants, active ingredients, and mixtures thereof, and
  f) optionally water,
wherein the surface tension of component b) is in the range of ±15 dyn/cm of the surface tension of component a) or corresponds to the surface tension of component a), and the sum of components a) to f) is 100 wt % relative to the total quantity of the foam composition. In other words, the surface tension of component b) is in the range of not less than about 15 dyn/cm below the surface tension of component a) and not more than about 15 dyn/cm above the surface tension of component a).

It was completely surprising that such alcoholic foam compositions, which preferably are suitable for skin and hand disinfection and which contain at least 52 wt % relative to the total quantity of the foam composition, can be dispensed as foam via standard pump-foam systems, without suffering spontaneous foam breaking because of the high alcohol concentration in the composition. In particular, it would have been expected of such high alcohol concentrations that the alcohol components of such foam compositions would act merely as a solvent at an alcohol concentration of higher than 50 wt %, whereby the surface-active effects of the surfactants and accordingly their foaming ability also would be lowered. Such effects were not observed, however. To the contrary, it was found that stable voluminous foams for disinfection purposes could be produced with the foam compositions according to the present invention in standard pump-foam systems.

According to the present invention, the surface tension of component b) preferably lies in the range of ≧20 to ≦40 dyn/cm. The surface tension of component b) includes all values and subvalues therebetween, especially including 22, 24, 26, 28, 30, 32, 34, 36 and 38 dyn/cm.

Preferably, the alcoholic foam composition contains, as component a), alcohols of the general formula

in which R denotes an aliphatic straight-chain or branched hydrocarbon group that has 1 to 8 carbon atoms and that can be contained alone or in mixtures in the foam according to the present invention.

Examples of such alcohols are methanol, ethanol, 1-propanol, 2-propanol, 1-butanol, isobutyl alcohol, tert-butyl alcohol, the amyl alcohols, 1-, 2-, 3-pentanol or neopentyl alcohol as well as 1-hexanol, ethanol being particularly preferred as component a).

Preferably, the foam composition contains at least 52 to 99 wt %, preferably 55 to 96 wt % and especially more than 65 wt % of ethanol. The amount of ethanol includes all values and subvalues therebetween, especially including 55, 60, 65, 70, 75, 80, 85, 90 and 95 wt %. As regards the disinfectant action, it is particularly advantageous for the alcoholic foams according to the present invention to contain more than 80 wt % of alcohol.

As component b), the foam compositions according to the present invention can contain respectively a surfactant or surfactant mixture, with the proviso that the surface tension of the surfactant or of the surfactant mixture contained in the foam composition lies within the range of ±15 dyn/cm of the surface tension of component a), meaning the alcohol component, or corresponds to the surface tension of component a).

Every surfactant or surfactant mixture that satisfies the foregoing proviso is suitable as component b) of the foam compositions. The total quantity of the surfactant or surfactant mixture is 0.5 to 20, preferably 1 to 10 and particularly preferably 2 to 5 wt % relative to the total quantity of the foam composition. The amount of surfactant or surfactant mixture includes all values and subvalues therebetween, especially including 1, 2, 4, 6, 8, 10, 12, 14, 16, and 18 wt %

Such surfactants are, among other substances, silicone compounds, such as dimethylpolysiloxanes, methylphenylpolysiloxanes, cyclic silicones as well as silicone compounds modified by amino, fatty acid, alcohol, polyether, epoxy, fluoro, glycoside and or alkyl groups. Preferred as silicone compounds according to the present invention are polysiloxane-polyether copolymers [INCI(CFTA): dimethicone copolyol], which are available from the company named Goldschmidt AG of Essen under the trade name ABIL®, especially polysiloxane-polyether copolymers of the B 88 product family, such as ABIL® B 8843, ABIL® B 8851, ABIL® B 8852, ABIL® B 8863, ABIL® B 88183 and ABIL® B 88184. Particularly preferably, the foam compositions according to the present invention contain, as component b), polysiloxane-polyether copolymers available under the trade name ABIL® B 8832 (bis-PEG/PPG-20/20 dimethicone).

As further suitable surfactants or surfactant mixtures there can be mentioned the group of fluoro surfactants, which can be present as component b) in the foams, either alone or as mixture of various fluoro surfactants, especially also as mixtures with polysiloxane-polyether copolymers. Such suitable surfactants are, for example, tetraalkylammonium perfluoroalkylsulfonates, preferably the tetraethylammonium perfluorooctanesulfonate that is commercially available under the trade name FLUORTENSIDE FT-248.

Furthermore, the foam compositions contain, as component c), at least one polyalkylene glycol, which can be present preferably in proportions of 0.01 to 3, especially 0.01 to 0.2 and particularly preferably 0.05 to 0.2 wt % relative to the total quantity of the foam composition. The amount of polyalkylene glycol includes all values and subvalues therebetween, specially including 0.05, 0.1, 0.5, 1, 1.5, 2, and 2.5 wt %. Preferred polyalkylene glycols according to the present invention are in particular polyethylene oxide homopolymers with a molecular weight of 100,000 to 8,000,000, which are available as commercial products on the market under the trademark Polyox®, such as Polyox® WSR N-10, Polyox® WSR N-80 (PEG-5M), Polyox® WSR N-750 (PEG-7M), Polyox® WSR N-3000 (PEG-14M), Polyox® WSR N-3333, Polyox® WSR-205 (PEG-14M), Polyox® WSR-1105, Polyox®) WSR N-12K, Polyox® WSR N-60K (PEG-45M) and Polyox® WSR-301.

The foam compositions contain optionally at least one foam stabilizer, which is present as component d) in the foam in a proportion of 0.01 to 20 wt %, preferably 0.5 to 3 wt % relative to the total quantity of the foam composition. The amount of foam stabilizer includes all values and subvalues therebetween, especially including 0.05, 0.1, 0.5, 1, 2, 4, 6, 8, 10, 12, 14, 16 and 18 wt %. Examples of suitable foam stabilizers are polysaccharides, especially xanthan gum, guar-guar, agar-agar, alginates and tyloses, cellulose ethers, such as carboxymethylcellulose, ethylcellulose, hydroxypropylcellulose, methylcellulose, cellulose mixed ethers, such as carboxymethylhydroxyethylcellulose, ethylhydroxyethylcellulose, methoxyhydroxyalkylcelluloses, methylhydroxyalkylcelluloses, such as methylhydroxyethylcellulose, methylhydroxypropylcellulose, methylhydroxybutylcellulose. Preferred according to the present invention are alkylcelluloses, especially methylcellulose and ethylcellulose that are commercially available under the trade names METHOCEL® and ETHOCEL®, Besides water, the alcoholic foams according to the present invention can, if necessary, contain auxiliaries, adjuvants and/or active ingredients, such as dyes, solubilizers, complexing agents, sequestering agents, light-protecting filters or perfumes and scents, pH regulators, stabilizers, preferably cetearyl alcohol and/or hydrogenated castor oils, such as trihydroxystearin, preservatives, antioxidants and/or oil-based or water-based care components as component e), especially in standard proportions of preferably 0.05 to 5 wt % relative to the total weight of the foams. The amount of additional components includes all values and subvalues therebetween, especially including 0.05, 0.1, 0.5, 1, 1.5, 2, 2.5, 3, 3.5, 4 and 4.5 wt %. These optional constituents of component e) can normally be present in proportions of 0 to 5 wt % relative to the total weight of the foam, but the person skilled in the art will choose the weight proportion of component e) such that no impairment of foam formation occurs.

In a preferred embodiment of the present invention, the foams contain 55 to 96 wt % of ethanol, 1 to 10 wt % of bis-PEG/PPG-20/20 dimethicone as silicone surfactant, 0.0 to 3 wt % of ethylcellulose polymer as stabilizer in combination with a PEG polymer, selected from PEG 7M to PEG 45M, preferably 0.05 to 2 wt %, whereby very effectively disinfecting foams with excellent stability are obtained in standard pump-foam systems. These amounts are given based on the total weight of the foam composition. The amount of ethanol includes all values and subvalues therebetween, especially including 60, 65, 70, 75, 80, 85 and 90 wt %. The amount of bis-PEG/PPG-20/20 dimethicone includes all values and subvalues therebetween, especially including 0.1, 0.5, 1, 2, 3, 4, 5, 6, 7, 8 and 9 wt %. The amount of ethylcellulose polymer includes all values and subvalues therebetween, especially including 0.1, 0.5, 1, 1.5, 2 and 2.5 wt %. The amount of PEG polymer includes all values and subvalues therebetween, especially including 0.1, 0.5, 1, and 1.5 wt %.

The alcoholic foams according to the present invention can be used particularly advantageously as disinfectants, for example as antiseptics for wound, skin, stools and sputum disinfection as well as instrument disinfection, as laundry and surface disinfectants and, particularly preferably according to the present invention, as skin and hand disinfectants.

The possible optional addition of nonvolatile antimicrobial substances in the foams is used in particular to intensify the disinfectant properties of the alcohol component. Of course, this depends on the area of application for which the foams are intended.

Antimicrobial substances can be present if necessary and can be used in the foams preferably alone or as combinations of a plurality of disinfectant active ingredients. Preferred are invert soaps, such as cationic surfactants, quaternary ammonium compounds, including benzalkonium chlorides or benzethonium chloride, biguanide compounds, such as chlorhexidine salts, phenol compounds, cresols, per compounds, iodine compounds, such as polyvidone iodine, organic acids, etc.

Nevertheless, the addition of such antimicrobial active ingredients may not be not necessary, since the foams have such a high alcohol concentration that the alcohol component functions as the disinfectant active ingredient on its own.

According to the present invention, care and/or moisturizing active ingredients, which can be contained optionally in the foams, especially for use of the foams as skin and hand disinfectants, are active ingredients that remain on the skin after evaporation of the alcohol component of the foam, for example standard skin-care substances such as dexpanthenol, glycerin, 1,2-propanediol, sorbitol, 1,3-butylene glycol, polyethylene glycol and other polyalcohols, hyaluronic acids, urea, chamomile extracts, alkoxylated cetyl alcohols and/or nonvolatile antimicrobial substances.

Since, (luring use as skin and hand disinfectants, the high alcohol proportion in the foams causes drying out of the treated skin areas during application, the use of at least one skin-care substance and/or one moisturizer is actually indispensable in daily practice with regard to frequent application of such disinfectants.

Also advantageous for the use of the foams for skin and hand disinfection is a constituent of natural plant tannins, such as ladies' mantle (*Alchemilla xanthochlora*, Rosaceae), tormentil rootstock (*Potentilla erecta*, Rosaceae), oak bark (*Quercus petraea* and *Quercus robur*, Fagaceae), ratanhia root (*Krameria lappacea* syn. *K. triandra*, Krameriaceae), witch hazel leaves (*Hamamelis virginiana*, Hamamelidaceae) and bilberries (*Vaccinium myrtillus*, Ericaceae) and natural synthetic tannins, such as Na bichlorophenylsulfamine, preferably in a proportion of 0.01 to 5 wt % of active substance relative to the total quantity of the foams. Of those, *Hamamelis virginiana* is particularly preferred as tannin. The amount of tannin includes all values and subvalues therebetween, especially including 0.05, 0.1, 0.5, 1, 1.5, 2, 2.5, 3, 3.5, 4 and 4.5 wt %.

Despite their high alcohol concentration, the foams are characterized by very good stability, and so stable disinfectant foams, especially for skin and hand disinfection, are made available by the present invention. Even without further additional antimicrobial adjuvants, these foams satisfy the standards

| DIN EN 1499 | Disinfecting hand washing |
| DIN EN 1500 | Hygienic hand disinfection | among others, and in addition have hepatitis B activity. The latter effect especially is particularly advantageous, since the hepatitis B virus, just as the HIV virus that is responsible for the spread of AIDS (acquired immune deficiency syndrome), is communicable but is more stable and more infectious than the HIV virus. Thus, all precautions against transmission of hepatitis B are also preventive against the HIV virus (see Deutsches Ärzteblatt 84, No. 18, p. B 874 of 30 Apr. 1987).

Since the foams according to the present invention can have alcohol concentrations of >70 vol % or 60 wt % relative to the total quantity of the foam, they also have virus activity against "naked" or nonenveloped viruses, such as polioviruses and adenoviruses, and so such alcoholic foams are of particular interest as a form of application, especially for skin disinfection.

It is also advantageous that the foams according to the present invention can be dispensed in particular as pump foams via standard pump-foam systems to the consumers for disinfection purposes, preferably for skin and hand disinfection, especially because such pump foams can usually be manufactured inexpensively and simply as aerosol-base foams. Examples include the commercially available pump-foam systems of companies such as Airspray (Netherlands), Keltec (Netherlands), Ophardt (Germany), Brightwell (United Kingdom) and Supermatic (Switzerland).

The foam compositions of the present invention can be obtained by mixing components a) to c) and optionally d), e) and/or f).

Foam compositions preferred according to the present invention (all data in wt % relative to the total quantity of the foam composition):

| | Example | | | | |
| | A | B | C | D | E |
|---|---|---|---|---|---|
| Alcohol or alcohol mixture | 55.0 | 60.0 | 70.0 | 80.0 | 90.0 |
| Polyethylene glycol homopolymer | 0.1 | 0.1 | 0.1 | 0.1 | 0.05 |
| Stabilizer | 0.2 | 0.2 | 0.2 | 0.2 | 0.1 |
| Surfactant or surfactant mixture | 3.0 | 3.0 | 4.0 | 4.0 | 3.0 |
| Water | 41.7 | 36.7 | 25.7 | 15.7 | 6.85 |

Foam compositions preferred according to the present invention for skin and hand disinfection (all data in wt % relative to the total quantity of the foam composition):

| | Example | | |
| | 1 | 2 | 3 |
|---|---|---|---|
| Ethanol | 55.0 | 80.0 | 90.0 |
| PEG-14M | 0.1 | 0.1 | 0.05 |
| Ethylcellulose | 0.2 | 0.2 | 0.1 |
| Bis-PEG/PPG-20/20 dimethicone | 3.0 | 4.0 | 3.0 |
| Demineralized water | 41.7 | 15.7 | 6.85 |

German patent application 10 2004 062 775.4 filed, Dec. 21, 2004, is incorporated herein by reference.

Numerous modifications and variations on the present invention are possible in light of the above teachings. It is therefore to be understood that within the scope of the appended claims, the invention may be practiced otherwise than as specifically described herein.

The invention claimed is:

1. An alcoholic foamable composition comprising:
a) 52 to 99 wt. %, relative to the total quantity of the foamable composition, of an alcohol or mixture of alcohols of formula R—OH wherein R denotes an aliphatic straight-chain or branched hydrocarbon group having 1 to 8 carbon atoms;
b) 0.5 to 20 wt. %, relative to the total quantity of the foamable composition, of at least one silicone surfactant selected from the group consisting of methylphenylpolysiloxanes, cyclic silicones, bis-PEG/PPG-20/20 dimethicone, PEG/PPG-14/4 dimethicone, PEG/PPG-4/12 dimethicone, PEG/PPG-20/20 dimethicone, and PEG/

PPG-20/6 dimethicone, wherein said at least one silicone surfactant is not fluorinated and the surface tension of said at least one silicone surfactant lies within the range of ±15 dyn/cm of the surface tension of component (a);

c) 0.01 to 3 wt. %, relative to the total quantity of the foamable composition, of at least one polyalkylene glycol;

d) optionally, 0.01 to 20 wt. %, relative to the total quantity of the foamable composition, of at least one foam stabilizer;

e) optionally, at least one member selected from the group consisting of cosmetic auxiliaries, adjuvants, active ingredients, and mixtures thereof; and f) optionally, water;

wherein said alcoholic foamable composition is in the form of a pump-foam formulation before it is foamed, said pump-foam formulation being capable of forming a stabilized pump-foam.

2. The alcoholic foamable composition according to claim 1, wherein the surface tension of component b) is ≧20 to ≦40 dyn/cm.

3. The alcoholic foamable composition according to claim 1, wherein component a) comprises at least one member selected from the group consisting of methanol, ethanol, 1-propanol, 2-propanol, and mixtures thereof.

4. The alcoholic foamable composition according to claim 1, wherein component a) is ethanol.

5. The alcoholic foamable composition according to claim 1, wherein at least 52 to ≦99 wt %, relative to the total quantity of the foam composition, of ethanol is contained in the foamable composition alone or as part of component a).

6. The alcoholic foamable composition according to claim 1, wherein greater than 60 wt %, relative to the total quantity of the foamable composition, of ethanol is contained in the foamable composition as component a).

7. The alcoholic foamable composition according to claim 1, wherein the at least one polyalkylene glycol is selected from polyethylene oxide homopolymers.

8. The alcoholic foamable composition according to claim 7, wherein one or more of the polyethylene oxide homopolymers are selected from the group consisting of PEG-5M, PEG-7M, PEG-14M, PEG-23M, PEG-45M, and PEG-90M.

9. The alcoholic foamable composition according to claim 1, wherein the at least one polyalkylene glycol is selected from polyethylene oxide homopolymers having a molecular weight of from 100,000 to 8,000,000.

10. The alcoholic foamable composition according to claim 1, wherein 0.01 to 10 wt %, relative to the total quantity of the foamable composition, of at least one foam stabilizer is contained in the foam as component d).

11. The alcoholic foamable composition according to claim 1, wherein component d) comprises an alkylcellulose.

12. The alcoholic foamable composition according to claim 1, comprising: 55 to 96 wt % of ethanol, 1 to 10 wt % of at least one of said silicone surfactants, 0.0 to 3 wt % of ethylcellulose polymer, and 0.05 to 2 wt % PEG polymer selected from the group consisting of PEG 7M to PEG 45M and mixtures thereof.

13. A disinfectant, comprising: the alcoholic foamable composition according to claim 1.

14. An antiseptic for wound, skin, stools and sputum disinfection or instrument disinfection, comprising: the alcoholic foamable composition according to claim 1.

15. A laundry and surface disinfectant, comprising: the alcoholic foamable composition according to claim 1.

16. A skin and hand disinfectant, comprising: the alcoholic foamable composition according to claim 1.

17. A method of disinfecting skin with a stabilized pump foam said method comprising:

applying a stabilized pump foam to the skin of a consumer, wherein stabilized pump foam is formed from the alcoholic foamable composition according to claim 1.

18. The method of claim 17, wherein the stabilized pump foam is applied to a hand of the consumer.

19. The method of claim 17, wherein component a) of the foamable composition is ethanol at a concentration of greater than 60 wt %, relative to the total quantity of the foam composition.

20. A method of dispensing a stabilized pump foam, said method comprising:

dispensing a stabilized pump foam from a pump-foam system, wherein the stabilized pump foam is formed from the alcoholic foamable composition according to claim 1.

21. A pump-foam system for dispensing a stabilized pump foam, said pump-foam system comprising:

the alcoholic foamable composition according to claim 1 to be dispensed via the pump-foam system.

* * * * *